US010827695B2

(12) United States Patent
John et al.

(10) Patent No.: US 10,827,695 B2
(45) Date of Patent: Nov. 10, 2020

(54) PROCESS FOR IN VITRO FLOWERING IN CROCUS SATIVUS L

(71) Applicant: Council of Scientific & Industrial Research, New Delhi (IN)

(72) Inventors: Chovumpurathu Kurian John, Maharashtra (IN); Mrudul Vijay Shirgurkar, Maharashtra (IN); Ashok Bhimrao Dhage, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 256 days.

(21) Appl. No.: 16/063,674

(22) PCT Filed: Dec. 16, 2016

(86) PCT No.: PCT/IN2016/050446
§ 371 (c)(1),
(2) Date: Jun. 18, 2018

(87) PCT Pub. No.: WO2017/103948
PCT Pub. Date: Jun. 22, 2017

(65) Prior Publication Data
US 2020/0120889 A1    Apr. 23, 2020

(30) Foreign Application Priority Data
Dec. 19, 2015    (IN) .......................... 4182/DEL/2015

(51) Int. Cl.
*A01H 5/02*    (2018.01)
*A01H 4/00*    (2006.01)
*A01H 6/12*    (2018.01)
*C12N 5/04*    (2006.01)
*C12N 5/00*    (2006.01)

(52) U.S. Cl.
CPC ............... *A01H 4/005* (2013.01); *A01H 6/12* (2018.05); *A01H 4/00* (2013.01); *A01H 5/02* (2013.01); *C12N 5/00* (2013.01); *C12N 5/0025* (2013.01); *C12N 5/04* (2013.01)

(58) Field of Classification Search
CPC .......... C12N 5/00; C12N 5/04; C12N 5/0025; A01H 4/00; A01H 4/005; A01H 5/02
USPC ..... 800/295, 298; 435/410, 420, 430, 430.1, 435/431
See application file for complete search history.

(56) References Cited

U.S. PATENT DOCUMENTS 5,085,995 A    2/1992    Otsuka et al.
5,217,897 A    6/1993    Kohda et al.

OTHER PUBLICATIONS royalqueenseeds.com/blog-splitting-stems-should-you-take-a-knife-to-your-cannabis-plant-n1207 downloaded on Apr. 27, 2020.*

Abdullaev F. et al. "Cancer Chemopreventive and Tumoricidal Properties of Saffrom (*Crocus sativus* L.)" *Exp Biol Med* 227: 20-25.
Basker D. et al., 1983 "Uses of Saffron," Economic Botany, vol. 37, No. 2, The New York Botanical Gaeden, pp. 228-236.
Chen S. et al., 2003 "Production of Crocin Using Crocus Sativus Callus by Two-Stage Culture System," Biotechnology Letters 25: 1235-1238.
Ebrahimzadeh H. et al., 2000 "In Vitro Productions of Floral Buds and Stigma-Like Structures on Floral Organs of Crocus Sativus L." *Pak J. Bot.*, 32(1): 141-150.
Fakhrai F. et al., 1990 "Morphogenlc Potential of Cultured Floral Explants of Crocus sativus L. for the In Vitro Production of Saffron" Journal of Experimental Botany, vol. 41, No. 222, pp. 47-52.
Himeno H. et al., 1988 "Scanning Electron Microscopic Study on the Vitro Organogenesis of Saffrom Stigma and Style-Like Structures," *Plant Science* 58: 93-101.
Hori H. et al., 1988 "Induction of Callus from Pistils of Crocus Sativus L. and Production of Color Compounds in the Callus," *Plant Tissue Culture Letters*, 5(2), 72-77.
Jun Z. et al., 2007 "Factors Influencing In Vitro Flowering from Styles of Saffrom," *Acta Hortic* 739: 313-320.
Koyama A et al.,1988 "Formation of Stigma-Like Structures and Pigment in Cultured Tissues of Crocus Sativus," *Planta Medica* 54: 375-376.
Loskutov A. V. et al., 1999 "Optimization of In Vitro Conditions for Stigma-Like-Structure Production From Half-Ovary Explants of Crocus Sativus L." *In Vitro Cell. Dev. Biol. Plant* 35:200-205.
Namin M., 2010 "Initiation and Origin of Stigma-Like Structures (SLS) on Ovary and Style Explants of Saffron in Tissue Culture," *ACTA Biologica Cracoviensia Series Botanica* 52(1): 55-60.
Sano K. et al., 1987 "In Vitro Proliferation of Saffron (*Crocus sativus* L.) Stigma," *Plant Cell, Tissue and Organ Culture* 11: 159-166.
Sarma K.S. et al., 1991 "Chemical and Sensory Analysis of Saffrom Produced Through Tissue Cultures of Crocus Sativus," *Plant Cell, Tissue and Organ Culture* 26:11-16.
Sarma L. S. et al., 1990 "In Vitro Production of Stigma-like Structures from Stigma Explants of Crocus Sativus L." Journal on Experimental Botany, vol. 41, No. 227, pp. 745-748.
Srivastava R. et al., 2010 "Crocus Sativus L.: A Comprehensive Review" Pharmacognosy Reviews, vol. 4, Issue 8, pp. 200-208.
Zeng et al., 2003 "Increased Crocin Production and Induction Frequency of Stigma-Likestructure from Floral Organs of Crocus Sativus by Precursor Feeding" *Plant Cell, Tissue and Organ Culture* 72: 185-191.
Mir et al. 2010 In vitro development of microcorms and stigma like structures in saffron (*Crocus sativus* L.) *Physiol Mol Biol Plants* 16(4):369-373.
Parray et al. 2012 "In vitro cormlet production of saffron (*Crocus sativus* L. *kashmirianus*) and their flowering response under greenhouse" *GM Crops & Food Biotechnology in Agriculture and the Food Chain* 3(4): 289-295.

(Continued)

*Primary Examiner* — Anne Marie Grunberg
(74) *Attorney, Agent, or Firm* — Knobbe, Martens, Olson & Bear, LLP

(57) ABSTRACT

A process for in vitro induction of flowering/in vitro proliferation of floral primordia in saffron crocus (*Crocus sativus* L.) produces whole flowers with real stigmas. The process produces saffron through a process of in vitro flowering to obtain season independent, continuous flowering of saffron.

13 Claims, 5 Drawing Sheets

(56) References Cited

OTHER PUBLICATIONS

Sheibani et al. 2006 "Induction of Somatic Embryogenesis in Saffron Using Thidiazuron (TDZ)" in *II International Symposium on Saffon biology and Technology* 739: 259-267.

* cited by examiner

PROCESS FOR IN VITRO FLOWERING IN *CROCUS SATIVUS* L

TECHNICAL FIELD OF THE INVENTION

The present invention relates to a process for in-vitro induction of flowering/in-vitro proliferation of floral primordia in saffron crocus (*Crocus sativus* L.) to produce whole flowers with real stigmas. More particularly, the present invention provides cost effective alternative to field cultivation of saffron, through season independent, continuous process of in-vitro induction of flowering/in-vitro proliferation of floral primordia to produce whole flowers with real stigmas of saffron crocus (*Crocus sativus* L).

BACKGROUND OF THE INVENTION

Saffron of commerce is the dried stigmas of saffron crocus (*Crocus sativus* L.), which has long been used as a spice, coloring agent and medicine. It has great commercial value and is the source of three high value phyto-chemicals crocin, picrocrocin and safranal. It is the most expensive spice in the world (Rs. 200,000 to 300,000 per Kg). Saffron phytochemicals possess a number of medicinally important activities such as anti-inflammatory, antioxidant, anticonvulsant, anxiolytic, antidepressant, aphrodisiac, antihypertensive, anti-tussive, anti-nociceptive, anti-genototoxic and cytotoxic effects (Kirtikar & Basu, 1933). They improve memory and learning skills, and increases blood flow in retina and choroid (Srivastava et al., 2010). Saffron phytochemicals also have anti-cancer and tumericidal properties (Abdullev, 2002).

At present saffron crocus is cultivated in a narrow geographical belt extending from Crete (Spain) in the West and Kashmir (India) in the East between tropical and temperate climate regions, because of the crops specific soil and climate requirement. Iran, Spain (together account for 80% of the world saffron production), India, Greece, Azerbaijan, Morocco are the major producers of saffron. In India, saffron is cultivated in Pampore (Kashmir) and Kishtawar (Jammu).

Though, India was one of the major producers of saffron along with Spain and Iran, the area under saffron cultivation and the annual production, however, have witnessed rapid and drastic declines in the past two decades. In view of the variety of biological activities and less availability of the raw material, the research on this valuable natural product has been hampered. Therefore, it is necessary to increase the produce of this valuable natural product, saffron, in a larger scale to meet the increasing global demand.

However, increasing saffron production by traditional means is difficult. The high cost of saffron may be attributed to three reasons: (i) specific agro-climatic requirement for cultivation, (ii) low yield, and (iii) labor intensive, manual harvesting. There has been very little improvement in the conventional cultivation practices followed for thousands of years. Though there have been many attempts to develop an alternative to saffron production by field cultivation, till today no such methods are available. Currently available methods for in-vitro proliferation of stigma tissue, and production of stigma like structures (SLS) from young flower bud, floral organs or their parts as explants have many limitations and are not commercially viable.

Sano et al.'s (1987) was one of the first who attempted to develop an alternative to the production of saffron through field cultivation. They worked on in vitro proliferation of stigma tissue and production of stigma like structures (SLS) (Sano & Himeno, 1987; Plessner & Ziv, 1999; Husaini et al., 2010). Sano & Himeno (1987) used intact stigmas plus ovary as explants. Young excised single stigmas or half ovaries were also cultured. They could achieve proliferation of stigma tissue as a callus (through indirect organogenesis) and also production of stigma like structures (SLS) (through indirect organogenesis). There are several reports on the production of stigma like structures (SLS) (Chen et al., 2003; Zeng et al., 2003; Jun et al., 2007; Mir et al., 2010; Namin et al., 2010). Sano & Himeno (1987) reported increased formation of pigmented stigma-like structures (SLS) in vitro from excised intact stigmas with ovary or half ovary as explants. Otsuka et al. (1992) reported production of stigma-like structures (SLS) in vitro when medium contained elevated levels of sucrose together with NAA, BA and alanine. The quality and quantity of saffron phytochemicals and pigments depended on the type of tissue or organs regenerated in vitro (Plessner & Ziv, 1999).

Stigma-like structures (SLS) regenerated from various flower organs contained low levels of saffron phytochemicals and pigments (Sano & Himeno, 1987) or altogether different phytochemicals and pigments. However, in some cases the composition and quantity of saffron phytochemicals and pigments were similar to that produced in stigmas harvested from plants grown naturally (Sano & Himeno, 1987; Plessner & Ziv, 1999; Husaini et at, 2010).

In-vitro proliferated callus tissue from stigma explants or in-vitro produced stigma like structures (SLS) from young flower buds, whole or part of floral organs (corolla, stamens, filaments, anthers, pistil, ovary, carpels, placenta, style, intact or excised stigmas) do not contain enough secondary metabolites. All the methods practiced until now in prior art use young flower buds, various floral organs such as corolla, stamens, filaments, anthers, pistil, ovaries, carpels, placentas, style and stigma etc. as explants to generate callus tissue (through indirect organogenesis) or stigma like structures (SLS) in an effort to increase the production of saffron spice. It is generally accepted in the field that real stigma from whole flowers expected to produce higher quality saffron than SLS. In this context inducing flowering is a desirable objective.

Further, roughly 150 flowers together yield 1 g (0.035 oz) of dry saffron threads. Therefore, to increase the yield of saffron, it is imperative to increase the number of flowers with stigmas possessing actual natural ingredients, which may be processed for producing saffron strands.

However, methods available until now are for the production of stigma like structures (SLS), and not for real stigmas. Further methods explored until now are not economically viable, for the production of saffron by field cultivation and are not suitable for commercial production of saffron as an industry, in view of relatively low content of pigment and aromatic compounds.

Therefore, to address the long standing need of the prior art to develop an alternative to increase saffron production at an economical scale, present inventors for the first time, have come-up with a season independent, continuous in vitro induction of flowering/in vitro proliferation of floral primordia process to produce whole flowers and real stigmas of saffron using dormant corms of the right size collected at the right time as explants unlike young flower buds or whole or part of floral organs.

OBJECTS OF THE INVENTION

The object of the present invention is to address the problems in the prior art by adopting a totally new approach for production of saffron whole flowers with real stigmas which is season independent and cost effective through in-vitro induction of flowering/in-vitro proliferation of floral primordial to increase the number of flowers/per field/year.

SUMMARY OF THE INVENTION

In the context of above mentioned lacunae in the prior art, the inventors of the present invention have developed a process comprising specific combinations and sequence of steps and thermodynamic treatments including choice of correct explant (plant part used as the starting material), choice of explant size according to diameter and weight, right time of explant lifting, surface sterilization of the explants, culture medium in which the right Plant Growth Regulators (PGR˜s) are used at their optimum concentrations, inoculation/incubation, etc. so as to successfully achieve for in-vitro induction of flowering/in-vitro proliferation of floral primordia.

Accordingly, the present invention provides season independent, continuous in-vitro induction of flowering/in vitro proliferation of floral primordia process to produce whole flowers with real stigmas of saffron crocus (Crocus sativus L) using dormant corm explant, comprising the steps of:
 a. Standardization of the right size of corm explants based on diameter and weight, and the right time for collection of the corm explants and initiation of cultures;
 b. Surface sterilization of corm explants by washing them with dilute detergent followed by treating with a suitable broad spectrum anti-microbial agent and several washings thereafter with distilled water;
 c. Preparation of the standardized basal media of Murashige—Skoog˜s (MS) with the major elements (N, P, K, Mg, Ca etc.) and minor elements (I, Na, Mn, Zn, Mo, Cu, Co, Fe etc.) supplemented with vitamins and PGRs at a concentration ranging from 0.01 to 2 mg/l, in liquid or semi-solid state; and
 d. Aseptic inoculation of the surface sterilized explants in/on to the MS medium of step (c), in a sterile work station in an inoculation room maintained at a high degree of sterility, and temperature of 25±2° C.;
 e. Incubation of the explants in an incubation room/growth chamber under sterile conditions at a temperature in the range of 9-30° C. (usually at 22±2° C., but with diurnal, and season dependant variations) with a photoperiod of about 16 hours at light intensity of 11.7 ≈ mol/m$^2$/s followed by about 8 hour dark period with RH of 50-90% until sprouts are formed; and
 f. Transferring and incubating the sprouted cultures slit vertically in/on the MS medium of step (c) to produce whole flowers with real stigmas.

DETAILED DESCRIPTION OF THE INVENTION

Figure 1:
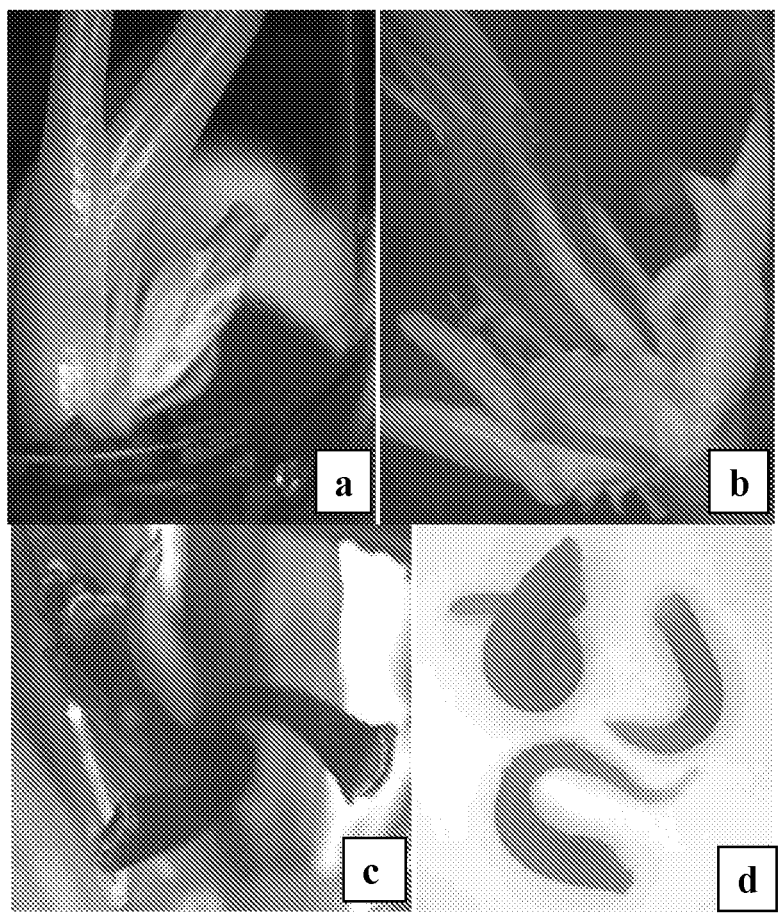
FIG. 1: depicts a. Whole flower (bud stage), b. Whole flower (open), c& d. Stigmas

The following description is illustrative of embodiments of the invention. The following description is not to be construed as limiting, it being understood, that the skilled person may carry out many obvious variations to the invention.

The present invention discloses a novel cost effective process for the in-vitro production of flowers in saffron crocus (Crocus sativus L.) by way of growth and development of pre-existing floral primordia, and extension of flowering season and production of multiple flowers through proliferation of these floral primordia Source of the explant: The corms of saffron crocus (Crocus sativus L.) were purchased from one saffron farmer in Pampore, Jammu & Kashmir, India and one saffron merchant in Srinagar, Jammu & Kashmir, India.

In an aspect, the invention relates to a process for production of whole flowers with real stigmas using dormant corms as explants where in flowering/proliferation of floral primordia is induced in vitro. This process takes the crop out of its basic requirement of specific soil and climatic conditions, and makes it season independent, wherein continuous production of saffron throughout the year and anywhere in the world is possible.

In an aspect of the process, the explant used as starting material is selected from corms (underground vegetative propagules), which are collected from soil at different times of the year (i.e. June to September), while they are still in dormant stage, to initiate the cultures. The corms are used in three different ways; (a) as entire corms, (b) corms cut horizontally or vertically at different levels, and (c) corms cut into small cube of about 1 cm$^3$ containing the dormant or slightly sprouted bud. The corms are of a size ranging from 0.5 cm to 2.5 cm in diameter 6 to 12 gm in weight.

The use of corm explants as a whole or when cut horizontally or vertically at different levels get contaminated and only 10 to 20% cultures remain sterile. Corms cut into small cube of about 1 cm$^3$ containing the dormant or slightly sprouted bud yield maximum sterile and sprouting cultures of about 50 to 80%.

In another aspect, the corm explants are sterilized using standardized multi-step surface sterilization process, with minimum damage to the explant, to obtain maximum sprouting cultures for flowering.

The sterilizing agents are selected from Labolene, Savlon (10 to 20%), Carnizim (1%), Bavistin (1%), Benomyl (2%), mercuric chloride (0.01% to 0.1%) and the like.

Accordingly, the sterilization comprises washing the corm explant with detergent Labolene (diluted 0.5-3 ml in 100 ml of water) for about 10 to 15 minutes. The explants are washed several times with distilled water to remove traces of the detergent. This is followed by treating with Savlon (10 to 20%) for 5 to 10 minutes and washing with distilled water. They are then treated with anti-fungal agent selected from Bavistin (1%) for 20 to 40 minutes or with Carnizim (1%) for 20 to 40 minutes or with Benomyl (2%) for 20 to 40 minutes and washed thoroughly with distilled water to remove any traces of anti-fungal agents. This is followed by treatment with mercuric chloride (0.01% to 0.1%) for about 5 to 8 minutes and washed with distilled water thoroughly. The treatment with mercuric chloride is given in a sterile work station.

The further aspect of the present in-vitro process includes aseptic inoculation of the sterilized explants on to the standardized media in a sterile work station at about 25° C.

The explants are either inoculated as whole or cut horizontally or vertically to a size ranging from 0.5 cm to 2.5 cm in diameter and 0.5 to 10 gm in weight or may be cut into small cube of about 1 cm$^3$ containing the dormant or slightly sprouted apical bud/s.

Different basal media selected include White˜s medium, Gambourg˜s B5 medium or basal medium of Murashige & Skoog (MS), either at full strength (100%) or half strength (50%), and/or in combination with major and minor nutrients of one medium with vitamins of another medium.

In a preferred aspect, the standardized basal media in accordance with the invention comprises Murashige & Skoog˜s (MS) basal medium either at full strength, or with the major elements (N, P, K, Mg, Ca etc.) at half strength (50%) and minor elements (I, Na, Mn, Zn, Mo, Cu, Co, Fe etc) at full strength (100%), and with vitamins of another basal medium, in liquid or semi-solid state. When used in semi-solid state, the medium comprises agar-agar in the range of 0.5 to 0.7% or other gelling agents.

The standardized basal medium further comprises plant growth regulators (PGRs) selected from synthetic auxins such as naphthaleneacetic acid, adenine-type cytokinins represented by BAP (6-benzylaminopurine), kinetin, and zeatin, phenylurea-type cytokinins like diphenylurea and thidiazuron (TDZ); Gibberellins (GA) at concentrations ranging from 0.01 to 5 mg/l. Preferably, the PGR˜s include BAP (6-benzylaminopurine), thidiazuron (TDZ) alone or in combination at concentration in the range of 0.01 to 5.0 mg/l.

The medium is dispensed in either in sterile culture bottles capped with polypropylene caps or in sterile test tubes plugged with cotton. The medium is autoclaved at 120° C.-125° C.; preferably at 121° C. and at pressure between 10-20 lbs; preferably 15 lbs for 10 to 30 minutes, preferably 20 minutes. The media is prepared in distilled water and the pH is adjusted in the range 5 to 6; preferably 5.6 to 5.8.

In a preferred aspect, the basal culture medium comprises Murashige and Skoog Medium (MS) either at full strength or with major elements N, P, K, Mg, Ca at half strength (50%) or with minor elements I, Na, Mn, Zn, Mo, Cu, Co, or Fe at full strength (100%); vitamins; 2% to 3% of sucrose as carbon source; PGR˜s selected from 6 benzyl amino purine (BAP) in the range of 0.5 to 2.0 mg/l or Thidiazuron (TDZ) in the range of 0.01 to 0.1 mg/l used separately; in liquid or semi-solid state.

The incubation of the cultures is carried out in a standard incubation room/growth chamber having controlled and standardized physical parameters such as sterile environment, temperature conditions, photoperiod, relative humidity (RH) and such conditions suitable/favourable for in-vitro induction of flowering in saffron. The present inventors observed that diurnal temperature variations are important for in-vitro induction of flowering/in-vitro proliferation of floral primordia in saffron.

Figure 2:
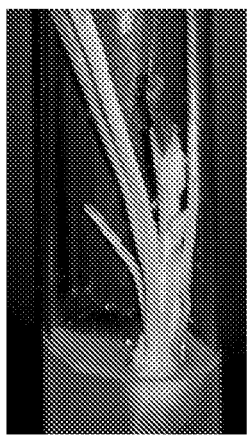
FIG. 2: depicts the in vitro induced flowering in Crocus sativus L.

Accordingly, the incubation is carried out at a temperature in the range of 9° C. to 30° C. preferably at a temperature in the range of 9° C. to 21° C., with RH (relative humidity) in the range of 50 to 90%, and photoperiod of about 16 hours provided by 1/2/4 cool fluorescent tubes (Philips, 40 W), giving about 11.7 ≈ mol m$^{-2}$ s$^{-1}$ PPF (Photosynthetic Photon Flux) i.e. ~866 lux (illuminance) each followed by 8-h dark period. The cultures are maintained for 4-5 weeks in the medium at above incubation conditions during which 80% of the culture remain sterile and show sprouting. They are then transferred to fresh MS medium of same composition and incubated under sterile conditions for about 1 to 2 weeks till the sprouted buds are about 8 cm long. The sprouted buds are slit vertically and incubated in MS medium of same composition for another 2 to 3 weeks under the same conditions. This helps the bud to open and grow further (FIG. 1 & FIG. 2).

Figure 3:
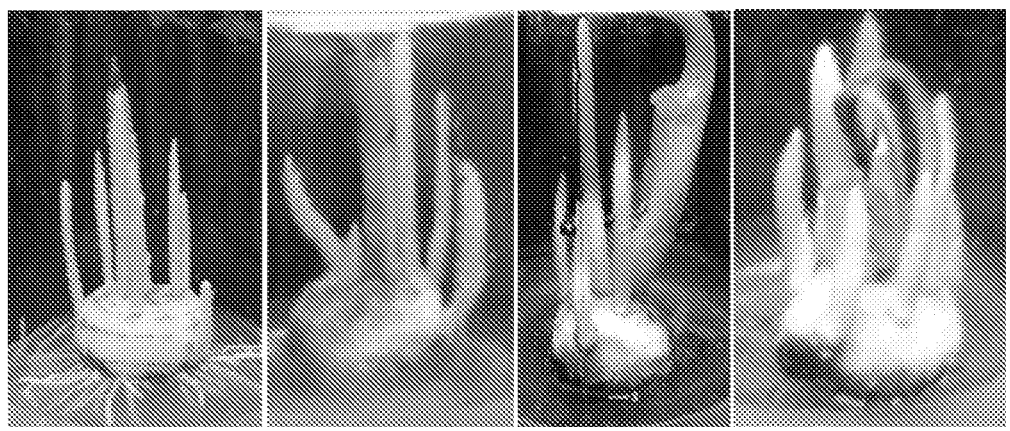
FIG. 3: depicts the effect of different concentration of BAP (i) Control (0); (ii) 0.5 mg/l BAP; (iii) 1.0 mg/l BAP; and (iv) 2.0 mg/l BAP
Figure 4:
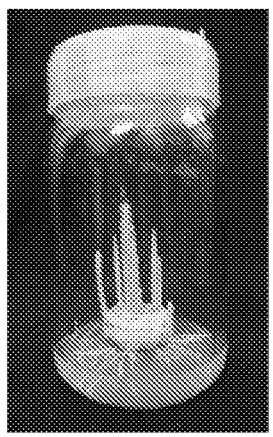
FIG. 4: depicts the in vitro culture of saffron on medium not containing PGRs.

In an aspect, about 50 to 70% of the cultures incubated in the MS medium of the above composition containing PGR˜s selected from 6 benzyl aminopurine (BAP) or Thidiazuron (TDZ) used individually at concentration in the range of 0.01 to 2.0 mg/L show presence of flowering buds as depicted in FIG. 3, whereas, the cultures incubated on medium with no PGR did not show emergence of the floral buds (FIG. 4).

The in-vitro induction of flowering/in vitro proliferation of floral primordia as per the process occurred in the month of December-January to February-March and until May which is generally not the flowering period for saffron.

The process according to the invention produced 1-8 flowers per culture vessel and on average 3-5 flowers per culture vessel. This was in difference to the naturally produced 2-3 flowers per corm/season.

Since each flower has three stigmas, 3-24 stigmas were produced per culture vessel. On the contrary, the corms usually yield 2-3 flowers and 3-9 stigmas/season (i.e. per year), in nature, in the period of 2-3 weeks from end of October to early to mid-November. The in-vitro induction of flowering/in vitro proliferation of floral primordia of the present invention yielded additional 3-15 stigmas in comparison to conventional field cultivation.

Thus according to the invention the number of stigmas/per corm/season was effectively 3 fold and occasionally 4 fold too. The inventors are further working in the field to standardize parameters for consistent yield of 8 flowers or even more per corm.

Further, the in-vitro production of flowers as per the present invention could be extended from mid-December to mid-May thus making the present in-vitro induction of flowering process continuous and season independent.

In an aspect, the saffron stigma produced by said in vitro technique in accordance with the invention finds use in the fields for food industry, dyeing and medicine as coloring, flavoring and aroma inducing agent for food stuffs, as a coloring agent for cotton and wool, and as a remedy for a number of diseases and health conditions.

The present in-vitro induction of flowering/in-vitro proliferation of floral primordia to produce whole flowers and real stigmas of saffron crocus (*Crocus sativus* L.) using corm explant allows season independent, year round production of saffron stigmas. With further refinement of the process the yield of saffron from one acre of the field may be obtained from approx. 1000-5000 sq. ft. of incubation room. The in-vitro induction flowering/in-vitro proliferation of floral primordia process of the present invention is an economical alternative to the production of saffron by field cultivation, and has high commercial potential.

The present process overcomes the dependence on climate and soil conditions thereby minimizing the uncertainty in the production of saffron flowers from corms in form of natural conditions, infestations which are beyond human control. This makes the process commercially scalable and can be carried out anywhere in the world not restricting to 'high temperature dip saffron producing zones_.

The industrial production of saffron has been an outstanding and unresolved problem for many decades. Induction of flowering (whole flower) of saffron in the laboratory and repeated flowering from the same corm has not been achieved till date.

In this invention, the inventors have arrived at a surprising combination & sequence of steps and thermochemical treatments which has for the first time enabled season independent flowering of saffron with the additional ability of producing multiple flowering events from the same corm. Thus, the inventors have achieved the ability to industrially produce saffron with increased stigma/corm/year. This will allow for high production in terms of saffron for a farmer compared to traditional practices.

Advantages of the Current Invention

The process makes saffron flowering season and region independent,
The process increases the number of flowers/corm/year.
The process increases the yield of stigmas (effectively saffron) from per hectare of field.
The stigmas (saffron) produced by this method have same ingredients as the naturally occurring stigmas. Quality of saffron is maintained.
The process of the invention takes 5-8 weeks only for complete flowering. The flowering is continuous and does not end with month of November unlike nature.
Method is an economical alternative to the production of saffron by field cultivation, and has high commercial potential.

EXPERIMENTAL METHODOLOGY

Experiments

To conduct the experiments, underground corms were procured from June to September 2014 from the saffron fields in Kashmir. Corms weighing 6-12 gms were used as the starting plant material. They were cleaned by removing soil and other extraneous material, and were stored under sterile sand at room temperature until used.

Example 1

Corms weighing ~10 gm were used for the experiments. Explants were prepared by trimming the sides and base of the corms and making small cubes of about 1 cm$^3$ containing the dormant or slightly sprouted apical buds on 22 Oct. 2014.

These explants were surface sterilized by washing them with neutral Detergent Labolene for 10 min followed by washing with 15% Savlon for 10 minutes. Further, these explants were treated with 1% Bavistin (BASF) for 30 minutes followed by 5 min followed by 0.08% mercuric chloride treatment in a sterile work station (Laminar Air Flow cabinet). After each treatment the explants were washed with sterile distilled water.

Preparation of Medium:

Murashige and Skoog Medium supplemented with 6 benzyl amino purine (BAP) (1.0 mg/l) was used for culture. The media made in distilled water was further constituted with 3% sucrose and 0.6% agar. The final pH was adjusted at 5.7. The media was autoclaved at 121° C. at 15 lbs pressure for 20 minutes.

The cultures were maintained for 5 weeks in the medium at 25±2° C., light intensity 16-h light (at 11.7 ≈ mol m$^{-2}$s$^{-1}$) followed by 8-h dark period.

The sterile sprouted buds of 5-7 cms length were transferred to fresh medium of same composition after making a vertical slit on the sprouting bud. It helps the bud to open and grow further.

They were again incubated for 3 weeks under the same incubation conditions.

Flowering was observed in the cultures by Nov. 5, 2014. This was the control experiment to ascertain and establish the viability of the medium created for in vitro flowering of saffron during the natural flowering season.

Preparation of Media not Having PGR:

For initiation of cultures Murashige and Skoog basal medium supplemented sucrose 3%, gelled with agar (0.6%) was used. No PGR was added and the final pH was adjusted at 5.7. Murashige and Skoog basal medium supplemented sucrose 3%, gelled with agar (0.5-0.7%) without PGRs was used as control. The media was autoclaved at 121° C. at 15 lbs pressure for 20 minutes.

These cultures were further incubated under the same incubation conditions for 4-5 weeks.

The sprouts on medium without PGRs were slender, the floral primordia were not developed further as in FIG. 4.

Example 2

Corms weighing ~10 gm were used for the experiments. Explants were prepared by trimming the sides and base of the corms and making small cubes of about 1 cm$^3$ containing the dormant or slightly sprouted apical buds on 22 Oct. 2014. One part of such samples was used for this set-up, while other was reserved for set up of Example 3.

The explants were surface sterilized by passing it through Detergent Labolene for 10 min followed by washing with 15% Savlon for 10 minutes. Further, the cubed explants were treated with 1% Bavistin (BASF) for 30 minutes followed by 5 min 0.08% mercuric chloride treatment in a sterile work station (Laminar Air Flow cabinet). After each treatment the explants were washed with sterile distilled water.

Preparation of Medium:

Murashige and Skoog Medium supplemented with 6 benzyl amino purine (BAP) (1.0 mg/l) was used for culture. The media made in distilled water was further constituted with 3% sucrose and 0.6% agar. The final pH was adjusted at 5.7. The media was autoclaved at 121° C. at 15 lbs pressure for 20 minutes.

The cultures were maintained for 5 weeks in the medium at 25±2° C. Light intensity 16-h light (at 11.7 ≈ mol m$^{-2}$ s$^{-1}$) followed by 8-h dark period.

The sterile sprouted buds of 5-7 cm length were transferred to fresh medium of same composition after making a vertical slit on the sprouting bud.

They were again incubated for 3 weeks under the same incubation conditions.

Initiation of flowering was observed in the culture until late December 2014 as in the FIG. 1.

Thus, following the experimental methodology as per the invention, the explants were observed to be flowering beyond their natural flowering period of October-November roughly.

The cultures were further maintained by transferring them on fresh medium of same composition and flowering was observed in the cultures until May 2015.

Examples 3

Second batch of explants of Example 2 was used to check the efficiency of TDZ.

Corms weighing ~10 gm were used for the experiments. Explants were prepared by trimming the sides and base of the corms and making small cubes of about 1 cm³ containing the dormant or slightly sprouted apical buds on 22 Oct. 2014.

The explants were surface sterilized by treating them with neutral detergent Labolene for 15 min followed by washing with 20% Savlon for 5 minutes. Further, the explants were treated with 1% Carnizim for 30 minutes followed by 0.05% Mercuric chloride treatment for 8 minutes in a sterile work station (Laminar Air Flow cabinet). After each treatment the explants were washed with sterile distilled water.

Preparation of Media Having TDZ

Murashige and Skoog basal medium+sucrose 2%, gelled with agar (0.7%) was supplemented with PGR Thidiazuron (TDZ)) at three concentrations viz. 0.01, 0.05, and 0.1 mg/l and the final pH was adjusted at 5.8. The media were autoclaved at 121° C. at 15 lbs pressure for 20 minutes.

The surface sterilized explants were inoculated on these media under aseptic conditions. The cultures were maintained for 5 weeks in the medium in an incubation room maintained at 25±2° C. during the day (temperature fell by 4-5° C. during the night in the winter), and 16 h light at an intensity of 11.7 $\approx$ mol m$^{-2}$ s$^{-1}$ followed by 8-h dark period.

The sterile sprouts of the cultures grown on medium with TDZ of 5-7 cms length were transferred to fresh medium of same composition after making a vertical slit on the sprouting bud in sterile work station. It helps the bud to open and grow further.

These cultures were further incubated under the same incubation conditions for 4-5 weeks. Flowering was observed by last week of December 2014.

The cultures were further maintained by transferring them on fresh medium of same composition and flowering was observed in the cultures incubated on TDZ containing medium till May 2015.

Example 4

Saffron (dried stigmas) from flowers produced in field cultivation from the same saffron field in Kashmir from where the corms were sourced for the experiments was compared with saffron (dried stigmas) from flowers developed in vitro by the process for in vitro induction of flowering/in vitro proliferation of floral primordia for phytochemical contents by HPLC analysis.

HPLC analytical conditions were as follows Reference Journal of Chromatography A, 664(1994) 55-61.

Figure 5A:
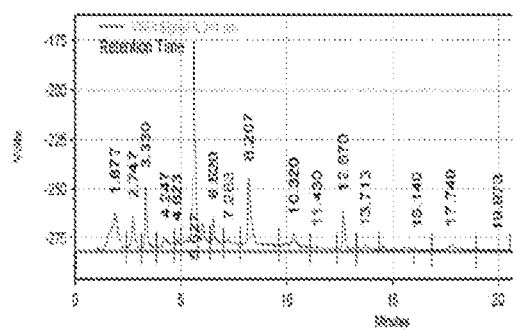
FIG. 5: HPLC analysis comparison of natural stigma from Kashmir (5(a)), stigma from flowers produced by the process (5(b))
Figure 5B:
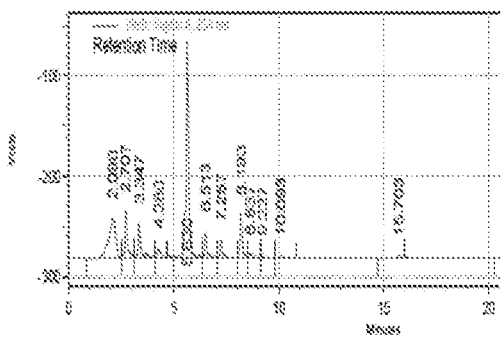

HPLC analysis indicated all peaks present in natural saffron sample from Kashmir (FIG. 5 (a)) were also present in sample from flowers developed in vitro FIG. 5(b).

It was concluded that saffron produced by the method described in the present invention contains crocin, picrocrocin and safranal. All these can be detected by uv at 254 nm.

The experimental set-up was repeated in subsequent years 2015, 2016 and was found to be reproducible as per the process of the invention.

REFERENCES

Abdullaev F I (2002). Cancer chemopreventive and tumoricidal properties of Saffron (*Crocus sativus* L.). *Exp. Biol. Med.* 227, 20˜25

Basker D & Negbi M (1983). Uses of saffron. *Econ. Bot.* 37, 228˜236

Chen Chen S., Wang X., Zhao B., Yuan X., Wang Y (2003). Production of crocin using *Crocus sativus* callus by two-stage culture system, *Biotechnol. Lett*, 25: 1235˜1238

Ebrahimzadeh H, Rajabian T & Karamian R (2000). In vitro production of floral buds and stigma-like structures on floral organ of *Crocus sativus* L. *Pakistan Journal of Botany* 32:134˜150.

Fakhrai F & Evans P K (1990). Morphogenic Potential of Cultured Floral Explants of *Crocus sativus* L. for the In Vitro Production of Saffron. *Journal of Experimental Botany*, 41(1):47-52.

Han L L & Zang X Y (1993). Morphogenesis of the style stigma like structures from floral explants of *Crocus sativus* L. and identification of the pigments. *Acta Botanica Sinica*, 35:157-160.

Himeno H, Matshima H & Sano K S (1988). Scanning electron microscopic study on the in vitro organogenesis of saffron stigma and style-like structures. *Plant Science* 58:93˜101.

Hori H, Enomoto K & Nakaya M (1988). Induction of callus from pistils of *Crocus sativus* L. and production of color compounds in the callus, *Plant Tissue Cult. Lett*, 5:72-77.

Husaini A M, Kamili A N, Wani M H, Teixeira da Silva J A & Bhat G N ((2010). Sustainable saffron (*Crocus sativus* Kashmirianus) production: Technological and policy interventions for Kashmir, *Functional Plant Science and Biotechnology*, 4:116-127.

Jia Y J, Chen F, Lin H H, Cao Y L, Li Y & Wang S (1996). Induction of style-stigma-like structure and regeneration of plantlets from corm of *Crocus sativus* in vitro. *J. Sichuan Univ. Nat. Sci. Edition* 33:747-750.

Jun Z, Xiaobin C & Fang C (2007) Factors influencing in vitro flowering from styles of saffron. *Acta Hortic*, 739: 313˜320

Kirtikar K R & Basu B D (1933). *Indian Medicinal Plants*, edited by L. M. Basu, 2nd ed., Allahabad: Central Council for Research in Ayurveda & Siddha, (Deptt. of AYUSH, Min. of Health & Family Welfare), Govt. of India.

Kohda H, Yamasaki K, Koyama A, Miyagawa H, Fujioka N, Omori Y, Ohta Y, Itoh H & Hosono T (1993) Process for Culturin Saffron Stigma Tissues. U.S. Pat. No. 5,217,897.

Koyama A, Ohmori Y, Fujioka N, Miyagawa H, Yamasaki K & Kohda H (1988). Formation of stigma-like structure and pigment in cultured tissues of *Crocus sativus*. *Planta Med*, 54:375-376.

Loskutov A V, Beninger C W, Ball T M, Hosfield G L, Nair M & Sink K C (1999) Optimization of in vitro conditions for stigma-like-structure production from half-ovary explants of *Crocus sativus* L. *In vitro. Cell Dev. Biol. Plant* 35:200˜205

Lu W L, Tong X R, Zhang Q & Gao W W (1992). Study on in vitro regeneration of style-stigma-like structure in *Crocus sativus* L. *Acta Bot. Sin.*, 34:251-256.

Mir J I, Ahmed N, Wani S H, Rashid R, Mir H & Sheikh M A (2010). In vitro development of microcorms and stigma like structures in saffron (*Crocus sativus* L.) *Physiol Mol Biol Plants*, 16(4):369˜373.

Namin M H, Ebrahimzadeh H, Ghareyazie B, Radjabian T & Namin H H (2010). Initiation and origin of stigma-like structures (sls) on ovary and style explants of saffron in tissue culture *Acta Biologica Cracoviensia Series Botanica* 52/1:55˜60, 2010.

Namera A, Koyoma N, Fujioka K, Yamasaki H & Konda H (1987). Formation of stigma like structures and pigments in cultured tissues of *Crocus sativus*. *Japanese Journal of Pharmcognosy*, 41:260˜262.

Otsuka M, Saimoto H S, Murata Y & Kawashima M (1992). Method for producing saffron stigma-like tissue and method for producing useful components from saffron stigma like tissue. U.S. Pat. No. 5,085,995, A28.08.89 U.S. Pat. No. 399,037, P 04.02.92.8 pp.

Sano K & Himeno H (1987) In vitro proliferation of saffron (*Crocus sativus* L.) stigma. *Plant Cell, Tissue and Organ Culture*, 11:159-166.

Sarma K S, Maesato K, Hara T & Sonoda Y (1990). In vitro production of stigma-like structures from stigma explants of *Crocus sativus* L. *Journal of Experimental Botany* 41:745-748.

Sarma K S, Sharada K, Maesto K, Hara T & Sonoda Y (1991). Chemical and sensory analysis of saffron produced through tissue cultures of *Crocus sativus*. *Plant Cell, Tissue and Organ Culture* 26:11-16.

Srivastava R, Ahmed H, Dixit R K, Dharamveer & Saraf S A (2010). *Crocus sativus* L.: A comprehensive review, *Pharmacogn. Rev.*, 4, 200-208.

Visvanath S, Ravishankar G A & Venkataraman L V (1990). Induction of crocin, crocetin, picrocrocin and safranal synthesis in calluscalture of saffron-*Crocus sativus* L. *Biotechnol. Applied Biochem*, 12:336-340.

Zeng Y, Yan F, Tang L & Chen F (2003). Increased crocin production and induction frequency of stigma-like-structure from floral organs of *Crocus sativus* by precursor feeding. *Plant Cell Tissue Organ Cult*, 72:185-191.

Zhao J, Chen F, Yan F, Tang L & Xu Y (2001) In vitro regeneration of style-stigma-like structure from stamens of *Crocus sativus*. Acta Bot. Sin. 43:475-479

We claim:

1. A season independent, continuous in-vitro induction of flowering to produce whole flowers with real stigmas of saffron crocus (*Crocus sativus* L) from dormant corms comprising;
   (a) providing the corms as a whole or cut into pieces containing a slightly sprouted bud,
   (b) surface-sterilizing the corms provided in (a) and incubating the surface sterilized corm explants under sterile conditions in Murashige and Skoog (MS) medium for a period of about 5-8 weeks;
   (c) transferring the culture to fresh MS medium and incubating under sterile conditions for about 1 to 2 weeks till the sprouted buds are about 7-8 cm long; and
   (d) incubating the sprouted buds after making a vertical slit on the sprout in the same MS medium under sterile conditions for 2-3 weeks to produce whole flowers with real stigmas;

wherein said incubation is carried out in an incubation room/growth chamber at a temperature in the range of 9-30° C. at a photosynthetic photon flux of 11.7 μmol m$^{-2}$ s$^{-1}$ under a photoperiod of about 16 hours and a Relative Humidity of 50-90% followed by an 8-h dark period in said MS culture medium which has sucrose as a carbon source and Plant Growth Regulators (PGR's).

2. The season independent, continuous in-vitro flowering process according to claim 1, wherein the PGR's are selected from 6 benzyl amino purine (BAP) or thidiazuron (TDZ).

3. The season independent, continuous in-vitro flowering process according to claim 1, wherein the PGR's are in a range of 0.01 to 2 mg/L.

4. The season independent, continuous in-vitro flowering process according to claim 1, wherein sucrose in the MS medium is in a range of 2-3%.

5. The season independent, continuous in-vitro flowering process according to claim 1, wherein the pH of the MS medium is in a range of 5.6-5.8.

6. The season independent, continuous in-vitro flowering process according to claim 1, wherein the MS medium is either at full strength, or with some elements thereof at half strength (50%) and other elements thereof at full strength (100%), and with vitamins for supporting plant cells.

7. The season independent, continuous in-vitro flowering process according to claim 1, wherein said MS medium optionally comprises 0.5% to 0.7% agar-agar.

8. The season independent, continuous in-vitro flowering process according to claim 1, wherein the incubation temperature is between 9-21° C.

9. The season independent, continuous in-vitro flowering process according to claim 1, wherein the flowering occurs from December until May.

10. The season independent, continuous in-vitro flowering process, according to claim 1, wherein the number of flowers produced per corm is in the range of 3-8.

11. The season independent, continuous in-vitro flowering process according to claim 6, wherein the elements at half-strength are selected from the group consisting of N, P, K, Mg and Ca.

12. The season independent, continuous in-vitro flowering process according to claim 6, wherein the elements at full-strength are selected from the group consisting of I, Na, Mn, Zn, Mo, Cu, Co and Fe.

13. The season independent, continuous in-vitro flowering process according to claim 1, wherein the corms are cut into cubes of approximately 1 cm$^3$.

* * * * *